United States Patent [19]
Axelsson et al.

[11] Patent Number: 5,360,809
[45] Date of Patent: Nov. 1, 1994

[54] IMIDAZOLE COMPOUNDS AND THEIR USE AS CALCIUM CHANNEL BLOCKERS

[75] Inventors: Oskar Axelsson; Dan Peters, both of Malmö, Sweden; Elsebet Ø. Nielsen, Copenhagen; Palle Christophersen, Ballerup, both of Denmark

[73] Assignee: NeuroSearch A/S, Denmark

[21] Appl. No.: 36,425

[22] Filed: Mar. 24, 1993

[30] Foreign Application Priority Data

Mar. 26, 1992 [DK] Denmark .................. 0401/92

[51] Int. Cl.$^5$ .................................. C07D 235/08
[52] U.S. Cl. .................................. 514/338; 514/322; 514/394; 546/199; 546/271; 548/304.4; 548/304.7; 548/306.1
[58] Field of Search .................. 546/271, 199; 548/304.4, 304.7, 306.1; 514/322, 338, 394

[56] References Cited

U.S. PATENT DOCUMENTS

| | | | |
|---|---|---|---|
| 4,492,708 | 1/1985 | Spitzer | 548/304.4 |
| 4,503,061 | 3/1985 | Bristol et al. | 514/338 |
| 4,550,119 | 10/1985 | Morrison | 514/394 |
| 4,734,415 | 3/1988 | Sircar et al. | 514/247 |
| 5,179,210 | 1/1993 | Ebel | 548/304.4 |
| 5,210,091 | 5/1993 | Axelsson et al. | 514/322 |

FOREIGN PATENT DOCUMENTS 186190  7/1986  European Pat. Off.

OTHER PUBLICATIONS

Khristich et al., Chemistry of Heterocyclic Compounds vol. 18, No. 12, pp. 1299–1302 (Jun., 1983).

Primary Examiner—Joseph Paul Brust
Assistant Examiner—Mary Susan H. Gabilan
Attorney, Agent, or Firm—Gordon W. Hueschen

[57] ABSTRACT

The present invention discloses compounds of the formula

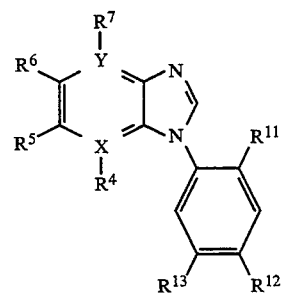

wherein

X is C;

Y is C;

$R^4$ to $R^7$ and $R^{11}$ to $R^{13}$ are as defined herein; or a pharmaceutically-acceptable addition salt thereof. The compounds are useful as pharmaceuticals, for example, in the treatment of stroke, ischemia, anoxia, migraine and psychosis.

9 Claims, No Drawings

IMIDAZOLE COMPOUNDS AND THEIR USE AS CALCIUM CHANNEL BLOCKERS

The present invention relates to therapeutically-active compounds and their use as well as to pharmaceutical preparations comprising the compounds. The compounds of the invention possess valuable activity as calcium channel blockers which make them useful in the treatment of anoxia, ischemia, psychosis, epilepsy, Parkinsonism, depression and migraine for example.

It is well known that an accumulation of calcium (calcium overload) in the brain is seen after anoxia, ischemia, migraine and other hyperactivity periods of the brain, such as after epileptic convulsions. An uncontrolled high concentration of calcium in the cells of the Central Nervous System (CNS) is known to cause most of the degenerative changes connected with the above diseases. Therefore compounds which can block the calcium channels of brain cells will be useful in the treatment of anoxia, ischemia, migraine, epilepsy and in the prevention of the degenerative changes connected with the same.

Compounds, partially or completely, blocking the so called L-type calcium channels in the CNS will be useful for the treatment of the above disorders by directly blocking the calcium uptake in the CNS.

Further, it is well known that the so called N- and P-types of calcium channels, as well as possibly other types of calcium channels, are involved in the regulation of neurotransmitter release. Compounds, partially or completely, blocking the N-and/or P-types of calcium channels will indirectly and very powerfully prevent calcium overload in the CNS after the hyperactivity periods of the brain as described above by inhibiting the enhanced neurotransmitter release seen after such hyperactivity periods of the CNS, and especially the neurotoxic enhanced release of glutamate after such hyperactivity periods of the CNS. Furthermore, blockers of the N- and/or P-types of calcium channels will as dependent upon the selectivity of the compound in question inhibit the release of various other neurotransmitters such as aspartate, GABA, glycine, dopamine, serotonin and noradrenaline. Therefore blockers of N- and/or P-types of calcium channels, as well as of possibly other types of calcium channels, may be useful in the treatment of psychosis, Parkinsonism, depression, epilepsy and other convulsive disorders.

It is an object of the present invention to provide compounds capable of partially or completely blocking the L-type and/or the N-type and/or the P-type of calcium channels, and/or other types of calcium channels.

The invention then, inter alia, comprises the following, alone or in combination:

A method of treating a disorder, which is responsive to the partial or complete blockade of calcium channels of the central nervous system of a living animal body, including a human, which comprises administering to such a living animal body, including a human, in need thereof a therapeutically-effective amount of a compound selected from those having the formula:

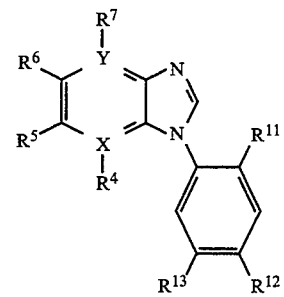

wherein
X is C or N;
Y is C or N;
$R^{11}$ is hydrogen, hydroxy, or alkoxy;
$R^{12}$ and $R^{13}$ are each independently hydrogen; halogen; $CF_3$; CN; OH; alkyl; cycloalkyl; cycloalkylalkyl; alkenyl; alkynyl; alkoxy; phenylalkyl; amino; nitro; sulphamoyl; pipiridyl; pyrrolidinyl; acyl; $CO_2H$; $CO_2$-alkyl; CO-amino; NH-CO-alkyl; phenylsulphonyl which may be substituted with halogen, $CF_3$, CN, OH, alkyl, alkenyl, alkynyl, alkoxy, amino, or nitro; phenyloxy which may be substituted with halogen, $CF_3$, CN, OH, alkyl, alkenyl, alkynyl, alkoxy, amino, or nitro; phenylamino which may be substituted with halogen, $CF_3$, CN, OH, alkyl, alkenyl, alkynyl, alkoxy, amino, or nitro; or aryl which may be substituted one or more times with halogen, $CF_3$, CN, OH, alkyl, cycloalkyl, cycloalkylalkyl, alkenyl, alkynyl, alkoxy, phenoxy, phenylalkyl, amino, nitro, sulphamoyl, pipiridyi, pyrrolidinyl, $CO_2H$, $CO_2$-alkyl, CO-amino, or NH-CO-alkyl; and $R^4$, $R^5$, $R^6$ and $R^7$ are each independently hydrogen; halogen; amino; nitro; CN; $CF_3$; COOH; COO-alkyl; alkyl; acyl; alkoxy; $-(CH_2)_n$-OH wherein n is 0, 1,2, or 3; $-(CH_2)_m$-O-alkyl wherein m is 0, 1,2, or 3; $-(CH_2)_o$-O-acyl wherein o is 0, 1,2, or 3;

and that if X is N then $R^4$ is absent and that if Y is N then $R^7$ is absent; or a pharmaceutically-acceptable addition salt thereof, and a method as above, wherein stroke, anoxia, ischemia, migraine, or epilepsy is treated, and a method as above, wherein psychosis, Parkinsonism, depression, epilepsy or any other convulsive disorder is treated, and a method as any above, wherein the compound employed is 1-[3-(3-aminophenyl)-phenyl]-5-trifluoromethyl-benzimidazole,
1-(3-phenylphenyl)-5-amino-benzimidazole,
1-[3-(3-amino-2-pyridyl)-phenyl]-5-trifluoromethyl-benzimidazole,
1-[3-(2-aminophenyl)-phenyl]-5-trifluoromethyl-benzimidazole,
1-[3-(4-methylphenyl)-phenyl]-benzimidazole,
1-[3-(3-aminophenyl)-phenyl]-benzimidazole,
1-[3-(3-methoxyphenyl)-phenyl]-5-amino-benzimidazole,
3-[(3-pyridyl)phenyl]-imidazo[5,4-b]pyridine,
1-[3-(1-imidazolyl)-phenyl]-5-trifluoromethyl-benzimidazole,
1-(3-phenylphenyl)-5-methoxy-benzimidazole,
1-[3-(3-chlorphenyl)-phenyl]-benzimidazole,
1-[3-(3-trifluoromethyl-phenyl)-phenyl]-benzimidazole,
or a pharmaceutically-acceptable addition salt thereof, and the method as any above, wherein the active ingredient is administered in form of a pharmaceutical composition thereof, in which it is present together with a pharmaceutically-acceptable carrier of diluent, further a method of preventing the degenerative changes connected with stroke, anoxia, ischemia, migraine, Parkinsonism, epilepsy or any other convulsive disorder, which comprises administering to a living animal body, including a human, in need thereof a therapeutically-effective amount of a compound as any above, further a compound having the formula

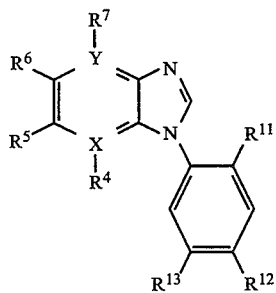

wherein
X is C or N;
Y is C or N;
$R^{11}$ is hydrogen, hydroxy, or alkoxy;
one of $R^{12}$ or $R^{13}$ is hydrogen; halogen; $CF_3$; CN; OH; alkyl; cycloalkyl; cycloalkylalkyl; alkenyl; alkynyl; alkoxy; phenylalkyl; amino; nitro; sulphamoyl; pipiridyl; pyrrolidinyl; acyl; $CO_2H$; $CO_2$-alkyl; CO-amino; NH-CO-alkyl; and the other of $R^{12}$ or $R^{13}$ is phenylsulphonyl which may be substituted with halogen, $CF_3$, CN, OH, alkyl, alkenyl, alkynyl, alkoxy, amino, or nitro; phenyloxy which may be substituted with halogen, $CF_3$, CN, OH, alkyl, alkenyl, alkynyl, alkoxy, amino, or nitro; phenylamino which may be substituted with halogen, $CF_3$, CN, OH, alkyl, alkenyl, alkynyl, alkoxy, amino, or nitro; or aryl which may be substituted one or more times with halogen, $CF_3$, CN, OH, alkyl, cycloalkyl, cycloalkylalkyl, alkenyl, alkynyl, alkoxy, phenoxy, phenylalkyl, amino, nitro, sulphamoyl, pipiridyl, pyrrolidinyl, $CO_2H$, $CO_2$-alkyl, CO-amino, or NH-CO-alkyl; and $R^4$, $R^5$, $R^6$ and $R^7$ are each independently hydrogen; halogen; amino; nitro; CN; $CF_3$; COOH; COO-alkyl; alkyl; acyl; alkoxy; $-(CH_2)_n$-OH wherein n is 0, 1,2, or 3; $-(CH_2)_m$-O-alkyl wherein m is 0, 1,2, or 3; $-(CH_2)_o$-O-acyl wherein o is 0, 1,2, or 3; and that $R^{12}$ is different from phenyl when X is C and $R^{11}$, $R^{13}$, $R^4$, $R^5$, $R^6$, and $R^7$ are each hydrogen;

and that if X is N then $R^4$ is absent and that if Y is N then $R^7$ is absent; or a pharmaceutically-acceptable addition salt thereof, and a compound as above which is
1-[3-(3-aminophenyl)-phenyl]-5-trifluoromethyl-benzimidazole,
1-(3-phenylphenyl)-5-amino-benzimidazole,
1-[3-(3-amino-2-pyridyl)-phenyl]-5-trifluoromethyl-benzimidazole,
1-[3-(2-aminophenyl)-phenyl]-5-trifluoromethyl-benzimidazole,
1-[3-(4-methylphenyl)-phenyl]-benzimidazole,
1-[3-(3-aminophenyl)-phenyl]-benzimidazole,
1-[3-(3-methoxyphenyl)-phenyl]-5-amino-benzimidazole,
3-[(3-pyridyl)phenyl]-imidazo[5,4-b]pyridine,
1-[3-(1-imidazolyl)-phenyl]-5-trifluoromethyl-benzimidazole,
1-(3-phenylphenyl)-5-methoxy-benzimidazole,
1-[3-(3-chlorphenyl)-phenyl]-benzimidazole,
1-[3-(3-trifluoromethyl-phenyl)-phenyl]-benzimidazole,
or a pharmaceutically-acceptable addition salt thereof, and further a pharmaceutical composition comprising an effective amount of a compound as any above, or a pharmaceutically-acceptable addition salt thereof, together with at least one pharmaceutically-acceptable carrier or diluent, as well as a method of preparing a compound having the formula

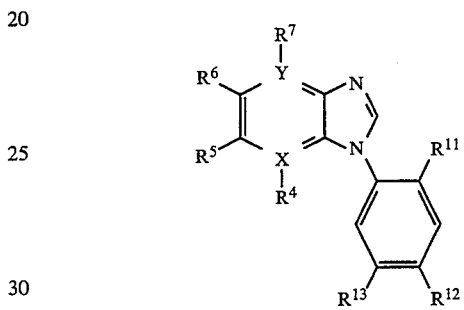

wherein
X is C or N;
Y is C or N;
$R^{11}$ is hydrogen, hydroxy, or alkoxy;
one of $R^{12}$ or $R^{13}$ is hydrogen; halogen; $CF_3$; CN; OH; alkyl; cycloalkyl; cycloalkylalkyl; alkenyl; alkynyl; alkoxy; phenylalkyl; amino; nitro; sulphamoyl; pipiridyl; pyrrolidinyl; acyl; $CO_2H$; $CO_2$-alkyl; CO-amino; NH-CO-alkyl; and the other of $R^{12}$ or $R^{13}$ is phenylsulphonyl which may be substituted with halogen, $CF_3$, CN, OH, alkyl, alkenyl, alkynyl, alkoxy, amino, or nitro; phenyloxy which may be substituted with halogen, $CF_3$, CN, OH, alkyl, alkenyl, alkynyl, alkoxy, amino, or nitro; phenylamino which may be substituted with halogen, $CF_3$, CN, OH, alkyl, alkenyl, alkynyl, alkoxy, amino, or nitro; or aryl which may be substituted one or more times with halogen, $CF_3$, CN, OH, alkyl, cycloalkyl, cycloalkylalkyl, alkenyl, alkynyl, alkoxy, phenoxy, phenylalkyl, amino, nitro, sulphamoyl, pipiridyl, pyrrolidinyl, $CO_2H$, $CO_2$-alkyl, CO-amino, or NH-CO-alkyl; and $R^4$, $R^5$, $R^6$ and $R^7$ are each independently hydrogen; halogen; amino; nitro; CN; $CF_3$; COOH; COO-alkyl; alkyl; acyl; alkoxy; $-(CH_2)_n$-OH wherein n is 0, 1,2, or 3; $-(CH_2)_m$-O-alkyl wherein m is 0, 1,2, or 3; $-(CH_2)_o$-O-acyl wherein 0 is 0, 1,2, or 3; and that $R^{12}$ is different from phenyl when X is C and $R^{11}$, $R^{13}$, $R^4$, $R^5$, $R^6$, and $R^7$ are each hydrogen; and that if X is N then $R^4$ is absent and that if Y is N then $R^7$ is absent; comprising:

a) the step of reacting a compound having the formula

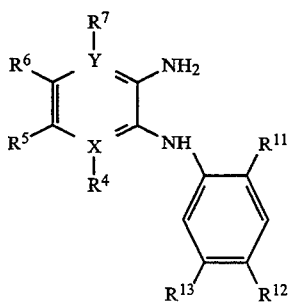

wherein X, Y, R¹¹, R¹², R¹³, R⁴, R⁵, R⁶, and R⁷ each have the meanings set forth above, with formic acid or a reactive derivative thereof to form a compound of the invention, or b) the step of reacting a a compound having the formula

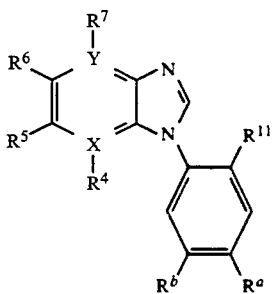

wherein X, Y, R¹¹, R⁴, R⁵, R⁶, and R⁷ each have the meanings set forth above and wherein one of R$^a$ and R$^b$ is iodine and the other of R$^a$ and R$^b$ is hydrogen, with R¹²-B(OH)₂ or R¹³-B(OH)₂, wherein R¹² and R¹³ have the meanings set forth above to form a compound of the invention.

A preferred value of one of R¹² and R¹³ is aryl which is substituted.

Halogen is fluorine, chlorine, bromine, or iodine; chlorine, bromine and iodine are preferred groups.

Alkyl means a straight chained or branched chain of from one to six carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Alkenyl means a group from two to six carbon atoms, including one double bond, for example, but not limited to ethylene, 1,2- or 2,3-propylene, 1,2-, 2,3-, or 3,4butylene.

Alkynyl means a group from two to six carbon atoms, including one triple bond, for example, but not limited to ethynyl, 2,3-propynyl, 2,3- or 3,4-butynyl.

Cycloalkyl means cycloalkyl of from three to seven carbon atoms, including cyclopropyl, cyclobutyl, cyclopentyl, cyclohexyl and cycloheptyl.

Cycloalkylalkyl means cycloalkyl as above and alkyl as above, meaning for example, cyclopropylmethyl.

Alkoxy means O-alkyl, wherein alkyl is as defined above.

Phenylalkyl means phenyl, and alkyl as above.

Acyl means CHO or CO-alkyl wherein alkyl is as defined above.

Amino means NH₂ or NH-alkyl or N-(alkyl)₂, wherein alkyl is as defined above.

Sulphamoyl means SO₂-amino, wherein amino is as defined above.

Aryl means a 5- or 6-membered monocyclic group. Such an aryl group includes, for example, phenyl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2, 4-thiadiazol 1,2,5-oxadiazol-3-yl, 1,2,5-oxadiazol-4-yl, 1,2,5-thiadiazol-3-yl, 1,2, 5thiadiazol-4-yl, 1-imidazolyl, 2-imidazolyl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl and tetrazolyl.

Examples of pharmaceutically-acceptable addition salts include inorganic and organic acid addition salts such as the hydrochloride, hydrobromide, phosphate, sulphate, citrate, lactate, tartrate, maleate, fumarate, mandelate, oxalate, benzoate, ascorbate, cinnamate, benzenesulfonate, methanesulfonate, stearate, succinate, glutamate, salicylate and the acetate. Such salts are formed by procedures well known in the art.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mandelates, or camphorsulphonate) salts for example. The compounds of the instant invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolution of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

Starting materials for the processes described in the present application are known or can be prepared by known processes from commercially available chemicals.

The products of the reactions described herein are isolated by conventional means such as extraction, crystallization, distillation, chromatography, and the like.

It has been found that the selectivity for the calcium channels, is dependent upon the degree of coplanarity of the aryl group, if actually present as a R¹² and/or $R^{13}$ substituent, with the phenyl ring to which it is attached, and it has been found that the selectivity and affinity for the blockade of the calcium channels can be affected by regulating the degree of the coplanarity of the aryl ring with the phenyl ring to which it is attached. The degree of this coplanarity is very sensitive to the substitution of the aryl ring, especially in the ortho position to the attachment atom to the phenyl ring. The degree of the coplanarity is thus suitably regulated by way of substituting the aryl ring of a compound of the invention or the phenyl ring to which it is attached. Suitable substituted aryl groups are, for example, 2-tetrazolylphenyl, 4-alkoxy-oxazol-2-yl, 4-alkoxy-1,2,5-thiadiazol-3-yl, 2-aminophenyl, 3alkoxyphenyl, 2-alkoxy-phenyl, 3-alkyl-2-thienyl, 3-alkoxy-2-furanyl, 3-cycloalkyl1,2,4-oxadiazol, 5-alkyl-3-isoxazolyl, 3-amino-2-pyridyl, and 1-alkyl-2-pyrrolyl.

Biology

A high influx of calcium from extracelluar compartments into neurons is seen after opening of voltage operated calcium channels. Such opening of calcium channels may be induced by depolarization of neuronal membranes. A crude synaptosome preparation contains small vesicles surrounded by neuronal membranes, and it is possible to study an opening of the voltage operated calcium channels in such a preparation. In the below described test influx of $^{45}Ca$ into rat synaptosomes is studied under depolarized conditions. The effect of test substances on the depolarization induced calcium uptake can thus be studied.

The calcium influx measured in this test is believed to represent the P- and L-type of calcium channels and compounds believed to block both the P- and the L-type of calcium channels will often exhibit a biphasic dose/response curve. The compounds of the present invention which potently block the calcium influx of up to 20 to 40% in this test are believed to be blockers of predominantly the P-type of calcium channels and the compounds of the present invention, which at somewhat higher concentrations block the calcium influx more completely or totally, are believed to be both P- and L-type calcium channel blockers, or predominantly L-type of calcium channel blockers.

Test Procedure

The cerebral cortex from a male Wistar rat is homogenized in 20 ml ice cold 0.32M saccharose. In the following steps the temperature is kept at 0° C. to 4° C. The homogenate is centrifuged at $1,000 \times g$ for 10 minutes and the supernatant recentrifuged for 20 minutes at $18,000 \times g$. The obtained pellet is resuspended in 0.32M saccharose (10 ml per g of original tissue). Aliquots of 0.05 ml of the hereby obtained synaptosome suspension are added to glass tubes containing 0.625 ml of a NaCl buffer (136 mM NaCl, 4 mM KCl, 0.35 mM $CaCl_2$, 1.2 mM $MgCl_2$, 20 mM Tris HCl, 12 mM glucose, pH 7.4) as well as 0.025 ml of different test substances in 48% ethanol. These tubes are pre-incubated for 30 minutes on ice and thereafter for 6 minutes at 37° C. $^{45}Ca$ uptake is initiated by addition to above glass-tubes of 0.4 ml $^{45}CACl_2$ (specific activity: 29–39 Ci/g; 0.5 Ci per tube). For depolarized samples the 0.4 ml $^{45}CaCl_2$ contain KCl (145 mM) and for non-depolarized NaCl (145 mM). The samples are incubated for 15 seconds. The $^{45}Ca$ uptake is stopped by filtering through glass fibre filters, which are subsequently washed 3 times with an ice cold solution of 145 mM KCl, 7 mM EGTA and 20 mM Tris HCl, pH 7.4 (5.0 ml). The radioactivity on the filters are measured by liquid scintillation spectrometry. Experiments are performed in duplicate.

Sample preparation

Above test substances are dissolved in, for example, 10 ml 48% ethanol at a concentration of 0.44 mg/ml. Dilutions are made in ethanol. Test substances are tested at concentrations of 0.1, 0.3, 1, 3, 10 ... μg/ml.

Results

Generally the compounds of the present invention in a low micromolar range (0.5 to 2μM) block 20 to 40% of the calcium influx measured in the above described test. Other compounds of the present invention also show the characteristics of L-type calcium channel blocking properties at somewhat higher concentrations.

TABLE

| Compound | $IC_{50}$ (μM) |
|---|---|
| 1-[3-(3-aminophenyl)-phenyl]-5-trifluoro-methyl-benzimidazole | 14 |
| 1-[3-(3-thienyl)phenyl-5-trifluoromethyl]-benzimidazole | 3.4 |
| 1-(4-iodophenyl)-5-fluoro-benzimidazole | 7.0 |

It has been found (electrophysiological studies using the patch-clamp technique as described by Hamill et al., Pflügers Arch. 391, 85–100 (1981)), that compounds of the invention block the N-type of calcium channels in a low micromolar range (0.3 to 3 μM). Examples of such compounds are 1-[3-(3-aminophenyl)-phenyl]-5-trifluoromethyl-benzimidazole, 1-(3'-N,N-diethylamino-biphenylyl)-5-trifluoromethyl-benzimidazole and 1-(3-iodophenyl)-5-trifluoromethyl-benzimidazole.

Some compounds of the invention also block the L-type calcium channels in electrophysiological studies.

Therefore the compounds are useful in the treatment of stroke, anoxia, ischemia and migraine (see also WO 91/07980).

Further it has been found that the compounds of the invention, and for example 1-[3-(3-aminophenyl)-phenyl]-5-trifluoromethyl-benzimidazole, potently (0.1 to 1 mg/kg) antagonize hypermotility in mice as induced by amphetamine or cocaine. These results are in fully accordance with the influence of N-type and P-type calcium channel blockers on transmitter release in the central nervous system.

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, one (1) to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In, tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated in solutions in aqueous polyethylene glycol solution.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

Due to the high degree of activity, the compounds of the invention may be administered to a subject, e.g., a living animal body, in need of alleviation, treatment, or amelioration of a disorder which is responsive to the activity or influence of the compounds of the present invention including responsive to the Ca channel blocking properties of the compounds of the invention. The compounds of the invention are preferably administered in the form of an acid addition salt thereof, concurrently, simultaneously, or together with a pharmaceutically-acceptable carrier or diluent, especially and preferably in the form of a pharmaceutical composition thereof, whether by the oral, rectal, or parenteral (including subcutaneous) route, in an effective amount. Suitable dosage ranges are 1–500 milligrams daily, preferably 1–100 milligrams daily, and especially 1–30 milligrams daily, depending as usual upon the exact mode of administration, form in which administered, the indication toward which the administration is directed, the subject involved and the body weight of the subject involved, and the preferences and experience of the physician or veterinarian in charge.

The following examples in the form of methods and in the form of tables according to which compounds of the invention have been prepared will illustrate the invention further; however they are not to be construed as limiting.

Method A

5-Cyano-1-(2-hydroxy-5-chlorophenyl)benzimidazole (1a) and 1-(2-hydroxy-5-chlorophenyl) benzimidazole-5-carboxylic acid (4a). A mixture of 2-amino-5'-chloro-4-cyano-2'-hydroxydiphenyl amine hydrochloride (1b) (1.00 g, 3.38 mmol), formic acid (3.1 g, 67 mmol), and 25% aqueous hydrochloric acid (20 ml) was refluxed for 1 h and then evaporated to dryness. Water (50 ml) and ethyl acetate (50 ml) was added and the mixture was stirred. The insoluble residue was separated by filtration and was found to be compound 1a. Yield: 300 mg, mp 308°–310° C. The organic phase was evaporated and compound 4a was isolated by column chromatography. Yield 70 mg, mp 330°–334° C.

Method B 1-(3-Iodophenyl)-5-trifluoromethylbenzimidazole (2a). A mixture of 2-amino-3'-iodo-4-trifluoromethyldiphenylamine (2b) (6.00 g, 14.4 mmol), formic acid (13.3 g, 289 mmol), and 25% aqueous hydrochloric acid (100 ml) was refluxed for 16 h. After evaporation to dryness, ethyl acetate (100 ml) and water (100 ml) was added. The organic phase was separated, dried and evaporated.

Method C

1(3'-Amino, 3-biphenylyl)-5-trifluoromethylbenzimidazole hydrochloride (8a). A mixture of 1-(3-iodophenyl)-5-trifluoromethylbenzimidazole (2a) (1.70 g, 4.38 mmol), 3-aminophenylboronic acid monohydrate (0.88 g, 5.69 mmol), tetrakis(triphenylphosphine)palladium(0) (150 mg, 0.13 mmol), 1M aqueous NaHCO$_3$ (13 ml, 13 mmol), and ethylene glycol dimethyl ether (26 ml) was refluxed under nitrogen with vigorous stirring for 2 h. After cooling to room temperature, ethyl acetate (100 ml) was added. The phases were separated and the organic phase was washed with water (2×30 ml). After removal of the solvent, the crude product was purified by chromatography on silica gel, first with methylene chloride, then with methylene chloride/methanol (19:1) as eluent. The product was then dissolved in diethylether and precipitated as the hydrochloride. Yield: 1.6 g (94%), mp 224°–226° C.

Method CC 1-(3'-Chloro-3,biphenylyl)-benzimidazole (23a). A mixture of 3-(1-benzimidazolyl)benzeneboronic acid (86a) (0.5 g, 2.1 mmol), 1-chloro-3-iodobenzene (0.55 g, 2.3 mmol), tetrakis(triphenylphosphine)palladium(0) (73 mg, 63 μmol), 1M aqueous NaHCO$_3$ (10 ml, 10 mmol), and ethylene glycol dimethyl ether (20 ml) was refluxed under nitrogen with vigorous stirring for 2 h. After cooling, ethyl acetate (100 ml) was added. The phases were separated and the organic phase was washed with water (2×30 ml). After removal of the solvent, the crude product was purified by chromatography on silica gel, first with methylene chloride, then with methylene chloride/methanol (19:1) as eluent. Yield: 0.55 g (70%), mp 70°–73° C.

Method D 1-(5-Chloro-2-hydroxyphenyl)-5-ethoxycarbonylbenzimidazole (6a). A mixture of 4a (170 mg, 0.59 mmol), conc. sulfuric acid (3 mg, 0.029 mmol), and 99% ethanol (10 ml) was refluxed for 1 h. Silica gel was added to the mixture and the solvent was evaporated. The silica gel containing the crude product was put on top of a silica gel column and the product was eluated by methylene chloride/ethanol (9:1). Yield 120 mg, mp>360° C.

Method E 1-(3'-N,N-Diethylamino-3-biphenylyl)-5-trifluoromethylbenzimidazole hydrochloride (10a). A mixture of compound 8a (0.75 g, 1.92 mmol), ethyl iodide (3.0 g, 19.2 mmol), potassium carbonate (2.6 g,19.2 mmol), and 99% ethanol (25 ml) was refluxed for 4 days. The solvent was evaporated and the crude product was purified by column chromatography, first with methylene chloride then with methylene chloride/methanol (19:1) as eluent. The product was then dissolved in diethyl ether and precipitated as the hydrochloride. Yield 350 mg, mp 109°–111° C.

Compound 13a was prepared in a similar way with 1,5-diiodopentane instead of ethyl iodide.

Method F

Step 1.

N-(3-Nitro-2-pyridyl)-N-formyl-3-aminophenylboronic acid.. A mixture of 2-chloro-3-nitropyridine (5.0 g, 32.2 mmol), 3-aminophenylboronic acid monohydrate (5.11 g, 32.2 mmol), sodium carbonate (13.7 g, 32.2 mmol), and DMF (100 ml) was stirred at 100° C. for 1 h. After cooling to room temperature, ethyl acetate (500 ml) was added and the solids were filtered off. The solution was transferred to a separatory funnel and washed with aqueous hydrochloric acid (3×200 ml, 1M). The organic phase was dried and the solvent removed. Yield 6.5 g, mp 242°–245° C.

Step 2.

N-(3-Amino-2-pyridyl)-N-formyl-3-aminophenylboronic acid hydrochloride was prepared from N-(3-nitro-2-pyridyl)-N-formyl-3-aminophenylboronic acid according to method T.

Step 3.

N-(3-Amino-2-pyridyl)-3-(3-pyridyl)aniline. A mixture of N-(3-amino-2-pyridyl)-N-formyl-3-aminophephenylboronic acid hydrochloride (0.80 g, 2.72 mmol), 3-bromopyridine (0.52 g, 3.35 mmol), tetrakis(triphenyl phosphine)palladium(0) (0.11 g, 0.10 mmol), 1M aqueous NaHCO3 (15 ml, 15 mmol), and ethylene glycol dimethyl ether (30 ml) was refluxed under nitrogen with vigorous stirring for 2 h. After cooling to room temperature, ethyl acetate (50 ml) was added and the phases were separated. The organic phase was washed with water (2×15 ml). The solvent was evaporated and the crude product was purified by column chromatography on silica gel with methylene chloride/methanol (9:1) as eluent. Yield: 0.60 g, mp 159°–160° C.

Step 4.

3-[(3-Pyridyl)phenyl]-imidazo-[5,4-b]pyridine (12a) was prepared from N-( 3-Amino-2-pyridyl)-3-(3-pyridyl)aniline according to method B.

In a similar way 3-(3',5'-dimethyl-3-biphenylyl)-imidazo-[5,4-b]pyridine (14a)was prepared from N-(3-amino-2-pyridyl)-N-formyl-3-aminophenylboronic acid hydrochloride and 1-bromo-3,5-dimethylbenzene via N-(3-amino-2-pyridyl)-3-(3,5-dimethylphenyl) aniline (oil).

Method G 1-(3'-Acetamido-3-biphenylyl)-5-trifluoromethylbenzimidazole (15a). Compound 8a (0.7 g, 1.79 mmol) was converted to the corresponding free base by partitioning between 0.1M aqueous NaOH (200 ml) and diethyl ether (200 ml). The phases were separated and the aqueous phase was extracted twice with ether. The combined ethereal phases were dried and evaporated. The residue was dissolved in dry methylene chloride (20 ml). Acetic anhydride (0.22 g, 2.15 mmol) was slowly added with ice cooling. After completed addition the mixture was stirred for one hour at room temperature. Methylene chloride (50 ml) and water (50 ml) was added and the aqueous phase was separated. The organic phase was dried and evaporated and the crude product purified by column chromatography, first with methylene chloride, then with methylene chloride/methanol (19:1), as eluent. Yield 400 mg, mp 118°–120° C.

Method H 1-(3-(1-Imidazolyl)-phenyl)-5 trifluoromethyl benzimidazole (49a). A mixture of 1-(3-iodophenyl)-5-trifluoromethyl-benzimidazole (2a)(1.0 g, 2.58 mmol), imidazole (0.19 g, 2.73 mmol), potassium carbonate (0.38 g, 2.78 mmol), CuBr (20 mg, 0.15 mmol), and 1-methyl-2-pyrrolidone was heated to 200° C. for 18 hours. Dilution with water and extractive workup with ether was followed by chromatography on silica gel. Yield: 0.43 g, 1.51 mmol, 51%. mp 177°–180° C.

Method I 1-(3-Hydroxyphenyl)-5-trifluoromethylbenzimidazole (80a). To an ice cooled solution of 1-(3-methoxyphenyl)-5-trifluoromethylbenzimidazole (79a)(0.50 g, 1.71 mmol) under nitrogen in dry methylene chloride (20 ml) was added boron tribromide (2.6 ml of an 1M solution in methylene chloride). The ice bath was removed and the reaction mixture was stirred for two days at room temperature, Dilution with water and extractive workup with ether was followed by chromatography. Yield: 0.29 g, 1.04 mmol, 61%. mp 168°–170° C.

Method J 1-(3-carboxamidophenyl)-5-trifluoromethylbenzimidazole (52a). A mixture of 1-(3-carboxyyphenyl)-5-trifluoromethyl-benzimidazole (100 mg, 0.3 mmol) and thionyl chloride (1 ml) was refluxed for 4 hours. The excess thionyl chloride was distilled off and the residue was dissolved in a few ml of THF, poured in conc. aqueous ammonia (30 ml) and stirred overnight. The crude product was filtered off and then purified by chromatography on silica gel. Yield: 50 mg, 0.16 mmol, 50%. mp 186°–187° C.

Method K 1-(3-biphenylyl)-5-hydroxymethylbenzimidazole (61a). To a solution of 1-(3-biphenylyl)-5-isopropoxycarbonylbenzimidazole (0.52 g, 1.6 mmol) in dry toluene (5 ml) under nitrogen at a temperature of $-70°$ C. was added diisobutylaluminum hydride (1.1 ml of an 1.5M solution in toluene). After 1.5 h at $-70°$ the reaction mixture was allowed to reach room temperature and was then poured in a slurry of 2M aqueous ammonium chloride and ice. After extractive workup with toluene the product was purified by chromatography on silica gel. Yield: 60 mg, 0.2 mmol, 12%. mp 130°–131° C.

Method L 1-(3-biphenylyl)-5-formylbenzimidazole (66a). To a solution of 1-(3-biphenylyl)-5hydroxymethylbenzimidazole (61a) (0.2 g, 0.7 mmol) in toluene (3 ml) was added benzeneseleninic acid (0.19 g, 1 mmol). The reaction mixture was heated to 85° C. for 2 hours. After cooling, the product was filtered off and washed thoroughly with warm water. Yield: 80 mg, 0.27 mmol, 38%. mp 170°–172° C.

Method M 1-(3-biphenylyl)-5-acetoxymethylbenzimidazole (68a). To a solution of 1-(3-biphenylyl)-5-hydroxymethylbenzimidazole (61a) (0.2 g, 0.7 mmol) in dry methylene chloride (5 ml) was added sodium carbonate (80 mg, 0.8 mmol) and acetyl chloride (568 µL, 0.8 mmol). The reaction mixture was stirred overnight. The mixture was filtered and the filtrate was evaporated to dryness. The product was obtained by crystallization from ethyl acetate/petroleum ether 1:1. Yield: 50 mg, 0.15 mmol, 21%. mp 190°–191° C.

Method N 1-(3-biphenylyl)-5-methoxymethyibenzimidazole (73a). To a solution of 1—(3-biphenylyl)-5-hydroxymethylbenzimidazole (61a) (0.16 g, 0.5 mmol) in dry DMF (1.5 ml) under nitrogen, was added a 80% sodium hydride suspension (20 mg, 0.7 mmol) and then iodomethane (33.5 µl, 0.5 mmol). The reaction mixture was stirred overnight and then poured in water. Neutralization with 4M aqueous HCl was followed by extraction with ethyl acetate. The extract was evaporated to dryness and purified by chromatography. The product was dissolved in dry ether and precipitated as the hydrochloride. Yield: 130 mg, 0.4 mmol, 80%. mp 70°–72° C.

Method O

1-[3-(3'-N,N-Diethylamino)biphenylyl]-benzimidazole hydrochloride (24a). To a solution of 1-[3-(3'-amino)biphenylyl]-benzimidazole hydrochloride (18a) (0.7 g, 2.17 mmol) and iodoethane (3.38 g, 21.7 mmol) in ethanol (50 ml) was added potassium carbonate (0.99 gmg, 7.18 mmol). The reaction mixture was refluxed for two days. The solvent was then evaporated and the product was purified by chromatography. It was then dissolved in dry ether and precipitated as the hydrochloride. Yield: 200 mg, 0.5 mmol, 24%. mp130°–132° C.

Method P

1-[3-(3'-amino)biphenylyl]-benzimidazole-5-carboxylic acid (29a). A solution of 3'(3-aminophenyl)-4-isopropoxycarbonyl-2-nitro-diphenylamine (800 mg, 2.0 mmol) in ethanol (25 ml) was hydrogenated over 5% palladium on charcoal (100 mg) at ambient pressure until no more hydrogen was absorbed. The suspension was filtered through celite and the filtrate was evaporated. Formic acid (10 ml) was added and the mixture was heated to reflux for 1 h. Water was added and the solid material was filtered off. This material was identified as 1-[3-(3'-formamido)biphenylyl]-benzimidazole-5-carboxylic acid isopropyl ester. It was dissolved in a mixture of ethanol (10 ml) and 4M aqueous sodium hydroxide solution (10 ml) and stirred at room temperature for three days. Neutralization with 2M aqueous sulfuric acid (10 ml) allowed the pure product to be filtered off. Yield: 200 mg, 0.5 mmol, 30%. mp>300° C.

Method Q 5-amino-1-(3-biphenylyl)benzimidazole hydrochloride (34a). A mixture of 2, 4-diamino-3'-phenyldiphenylamine hydrochloride (1.5 g, 4.8 mmol) and formic acid (10 ml) was added and the mixture was heated to reflux overnight. The pH was adjusted to 9 by the addition of aqueous sodium hydroxide. Extraction with ethyl acetate was followed by drying and evaporation. The solid residue was dissolved in a mixture of ethanol (10 ml) and 4M sodium hydroxide and stirred under nitrogen overnight. Dilution with water and extraction with methylene chloride gave, after drying and addition of HCl,the product as the hydrochloride. Yield: 700 mg, 2.1 mmol, 45%. mp 247°–249° C.

Method R 3-(3-Biphenylyl)imidazo[5,4-b]pyridine (39a)and 1-(3-biphenylyl)imidazo[4,5b]pyridine oxalate (88a).

A mixture of imidazo[4,5-b]pyridine (595 mg, 5 mmol), 3-bromobiphenyl (1.16 g, 5 mmol), potassium carbonate (1.03 g, 7.5 mmol), and copper powder (2.0 g) in N-methylpyrrolidone (10 ml) was heated to 200° under nitrogen for 4 h. After dilution with ethyl acetate the mixture was filtered through celite. Water was added and the phases were separated. After two more extractions with ethyl acetate the combined organic phases were dried and evaporated to give a light brown oil. Column chromatography on silica gel gave the two products as separate fractions with 1-(3biphenylyl-)imidazo[4,5-b]pyridine being the more polar one. This product was precipitated as the oxalate. Yield: 100 mg, 0.3 mmol, 5%. mp 174°–176° C. Yield of 3(3-biphenylyl-)imidazo[5,4-b]pyridine: 270 mg, 1 mmol, 20%. mp 89°–91° C.

Method S

5-Amino-1-(3'-methoxy-3-biphenylyl)-benzimidazole hydrochloride (56a). A mixture of 1-(3'-methoxy-3-biphenylyl)-5-nitrobenzimidazole (1.5 g, 4.9 mmol), tin(ll)chloride (2.7 g), conc. hydrochloric acid (20 ml), and ethanol (10 ml) was refluxed for 2 hours and then neutralized by the addition of concentrated ammonia and filtered through celite. The filter cake was washed with ethanol and then methylene chloride. The phases of the filtrate were separated and the aqueous phase was extracted twice with methylene chloride. The combined organic phases were washed with water, dried and the product was precipitated as the hydrochloride. Yield: 1.5 g, 4.3 mmol, 88%. mp 195°–200° C. (decomposition).

Method T

2-Amino-5'-chloro-4-cyano-2'-hydroxydiphenylamine hydrochloride (1b). A mixture of 1c (3.60 g, 12.4 mmol) and 5% palladium on charcoal in 99% ethanol (100 ml) was hydrogenated at ambient pressure until 895 ml hydrogen had been taken up. The reaction mixture was filtered through celite into methanolic hydrogen chloride (50 ml, 4.6M). The solvent and the excess hydrogen chloride were removed by evaporation to leave the product as a green solid. Yield 3.6 g, mp 170°–172° C.

Method U

2-Amino-3'-iodo-4-trifluoromethyldiphenylamine hydrochloride (2B). A mixture of 3B (6.0 g, 14.7 mmol), sodium sulfide hydrate (9.8 g, 44 mmol), ammonium chloride (2.35 g, 44 mmol), and 99% ethanol (100 ml) was refluxed under nitrogen for 3 hours. After cooling to room temperature the crude reaction mixture rapidly passed through a column of silica gel, using methanol as the eluent. The product was converted to the hydrochloride by the addition of methanolic hydrogen chloride followed by evaporation of the solvent. Yield 6.0 g, mp 182°–185° C.

Method V

Step 1.
4-Fluoro-3-nitrobenzonitrile. The largest amount of silica gel that still allowed the resulting slurry to be stirred magnetically at 0° C., was added to conc. sulfuric acid (125 ml). To this mixture 4-fluorobenzonitrile (12.5 g, 103 mmol) was added followed by potassium nitrate (10.4 g, 103 mmol). The reaction mixture was stirred at 0° C. for 20 minutes. The sulfuric acid was removed from the product by passing the mixture through a short column of silica gel and the product was washed out with methylene chloride. The solvent was evaporated to leave the product as a crystalline solid. Yield 6.0 g, mp 86°–88° C.

Step 2.
1-(4-Cyano-2-nitrophenyl)-benzoxazol-2-one. To a mixture of 4-fluoro-3-nitrobenzonitrile (3.90 g, 23.5 mmol) and 5-chlorzoxazone (3.98 g, 23.5 mmol) in dry DMF (40 ml) under nitrogen, was added sodium hydride (0.85 g, 28.2 mmol) over a period of 30 minutes, while keeping the temperature below 10° C. with an ice bath. The ice bath was removed and the mixture was stirred at room temperature for 1 h. The mixture was poured into water (200 ml) and the precipitate was collected by filtration. Yield 6.1 g, mp 228°–230° C.

Step 3.
5'-chloro-4-cyano-2'-hydroxy-2-nitrodiphenylamine (1c). A mixture of 1-(4-cyano-2-nitrophenyl)-benzoxazol-2-one (5.0 g, 15.8 mmol), aqueous NaOH (63.3 mmol, 4M), and ethylene glycol dimethyl ether (250 ml) was stirred at 50° C. for 2 h. After cooling to room temperature the inorganics were removed by passing the mixture through a silica gel column and the product was washed out with methanol. The solvent was evaporated to leave the product as a crystalline solid. Yield 4.5 g, mp 210°–212° C.

Method Xa

3'-Iodo-2-nitro-4-trifluoromethyldiphenylamine (2c). To a mixture of 3-iodoaniline (11.0 g, 50 mmol) and 4-chloro-3-nitrobenzotrifluoride (11.3 g, 50 mmol) in dry DMF (50 ml) under nitrogen, was added sodium hydride (2.55 g, 85 mmol) in small portions over 0.5 h. The reaction mixture was stirred at room temperature for 12 hours. The mixture was poured in water (200 ml). Diethyl ether (300 ml) was added and the phases were separated. The ethereal phase was washed with water (3×200 ml), dried and evaporated. The crude product was purified by column chromatography using petroleum ether/methylene chloride (4:1) as eluent. The crystalline product was triturated with petroleum ether and filtered. Yield 12.6 g, mp 98°–101° C.

Method Xb. Method Xb is the same as Method Xa but without solvent, with dry potassium carbonate as base and a reaction temperature of 180° C.

Method Xc. Method Xc is the same as Method Xa but with dry potassium carbonate as base and a reaction temperature of 120° C.

Method Y

1-[(6-Amino-2-pyridyl)-3-phenyl]-5-trifluoromethylbenzimidazole hydrochloride (43a). A solution of the amide 42a (0.6 g, 1.5 mmol) was refluxed in 25% aqueous hydrochloric acid (50 ml) for 15 h. The mixture was then evaporated to dryness and the crude product was triturated with ether. Yield: 0.55 g, 94%, mp 263°–264° C.

TABLE 1

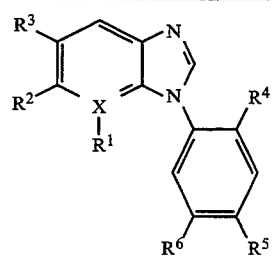

| No. | R¹ | R² | R³ | R⁴ | R⁵ | R⁶ | X | mp/°C. | Starting material | method |
|---|---|---|---|---|---|---|---|---|---|---|
| 1a | H | H | CN | OH | H | Cl | C | 330–334 | 1b | A |
| 2a | H | H | CF₃ | H | H | I | C | 86–87 | 2b | B |
| 3a | H | H | CF₃ | H | H | 3-Thienyl | C | 90–92 | 2a | C |
| 4a | H | H | COOH | OH | H | Cl | C | 308–310 | — | A |
| 5a | H | H | F | H | I | H | C | 60–62 | 5b | B |
| 6a | H | H | COOEt | OH | H | Cl | C | >360 | 4a | D |
| 7a | H | H | F | H | 3-Thienyl | H | C | oil | 5a | C |
| 8a* | H | H | CF₃ | H | H | 3-aminophenyl | C | 224–226 | 2a | C |
| 9a | H | H | CF₃ | H | H | 3-nitrophenyl | C | 140–142 | 2a | C |
| 10a* | H | H | CF₃ | H | H | 3-(diethylamino)phenyl | C | 109–111 | 8a | E |
| 11a | H | H | CF₃ | H | H | 4-bromophenyl | C | 115–117 | 2a | C |
| 12a | H | H | H | H | H | 3-pyridyl | N | 232–235 | — | F |
| 13a* | H | H | CF₃ | H | H | 3-(1-piperidyl)phenyl | C | 187–189 | 8a | E |
| 14a | H | H | H | H | H | 3,5-dimethylphenyl | N | oil | — | F |
| 15a | H | H | CF₃ | H | H | 3-acetamidophenyl | C | 118–120 | 8a | |
| 16a | H | H | CF₃ | H | H | phenoxy | C | 93–94 | 16b | B |
| 17a | H | H | H | H | H | I | C | oil | 17b | B |
| 18a* | H | H | H | H | H | 3-aminophenyl | C | 215–217 | 17a | C |
| 19a | H | H | CF₃ | OMe | H | OMe | C | 109–110 | 19b | B |
| 20a* | H | H | CF₃ | H | H | 2-aminophenyl | C | 228–231 | 2a | C |
| 21a | H | H | H | H | H | 3-trifluoromethylphenyl | C | oil | 17a | C |
| 22a# | H | H | H | H | H | 2-(N,N-dimethylamino)methylphenyl | C | 80–83 | 17a | C |
| 23a | H | H | H | H | H | 3-chlorophenyl | C | 73–75 | 86a | CC |
| 24a | H | H | H | H | H | 3-(N,N-diethylamino)phenyl | C | 130–132 | 18a | O |
| 25a | H | H | H | H | H | 4-acetamidophenyl | C | 70–73 | 86a | CC |
| 26a | H | H | CF₃ | H | H | phenethyl | C | 67–69 | 26b | B |
| 27a | H | H | H | H | H | 4-tolyl | C | oil | 17a | C |
| 28a | H | H | H | H | H | 4-aminophenyl | C | 156–158 | 25a | Y |
| 29a | H | H | COOH | H | H | 3-aminophenyl | C | >300 | — | P |
| 30a# | H | H | CF₃ | H | H | 2-(N,N-dimethylamino)methyl | C | 68–70 | 87a | CC |
| 31a | H | H | CF₃ | H | H | 3-pyridyl | C | 113–115 | 87a | CC |
| 32a | H | H | CF₃ | H | H | 4-(N,N-diisopropylamino)phenyl | C | 85–87 | 87a | CC |
| 33a | H | H | CF₃ | H | H | 4-acetamidophenyl | C | 198–200 | 87a | CC |
| 34a* | H | H | NH₂ | H | H | phenyl | C | 247–249 | 34b | Q |
| 35a* | H | H | CF₃ | H | H | 4-aminophenyl | C | 252–253 | 33a | Y |
| 36a | H | H | H | H | H | 3-ethoxycarbonylphenyl | C | oil | 17a | C |
| 37a | H | H | CF₃ | H | H | 3-(6-acetamidopyridyl) | C | 239–240 | 87a | CC |
| 38a* | H | H | CF₃ | H | H | 3-(6-aminopyridyl) | C | 292–294 | 37a | Y |
| 39a | H | H | H | H | H | phenyl | N | 89–91 | – | R |
| 40a | H | H | CF₃ | H | H | 4-tolyl | C | 145–147 | 2a | C |
| 41a | H | H | H | H | H | phenyl | C | oil | 17a | C |
| 42a | H | H | CF₃ | H | H | 2-(6-acetamidopyridyl) | C | 212–214 | 87a | CC |
| 43a* | H | H | CF₃ | H | H | 2-(6-aminopyridyl) | C | 263–264 | 42a | Y |
| 44a | H | H | H | H | H | 4-chlorophenyl | C | 137–138 | 17a | C |
| 45a | H | H | CF₃ | H | H | 4-trifluoromethylphenyl | C | 102–104 | 87a | CC |
| 46a | H | H | CF₃ | H | H | phenyl | C | 113–115 | 2a | C |
| 47a* | H | H | CH₃ | H | H | 3-aminophenyl | C | 270–273 | 81a | C |
| 48a | H | H | CF₃ | H | H | Br | C | 72–73 | 48b | B |
| 49a | H | H | CF₃ | H | H | 1-imidazolyl | C | 177–180 | 2a | H |
| 50a | H | H | CF₃ | H | H | hydroxy | C | 168–170 | 79a | I |
| 52a | H | H | CF₃ | H | H | carboxamido | C | 186–187 | 83a | J |
| 53a* | H | CH₃ | H | H | H | 3-aminophenyl | C | 202–204 | 82a | C |
| 54a* | H | H | CF₃ | H | H | 3-(5-aminopyridyl) | C | 200–202 | 87a | Y |
| 55a | H | H | CF₃ | H | H | 3-methoxyphenyl | C | 78–80 | 2a | C |
| 56a* | H | H | NH₂ | H | H | 3-methoxyphenyl | C | 190–200(d) | 84a | S |
| 57a | H | H | NO₂ | H | H | 3-aminophenyl | C | 213–215 | 85a | C |
| 58a | H | H | CF₃ | H | H | CH₃ | C | 109–110 | 58b | B |
| 59a | H | H | CF₃ | H | H | NO₂ | C | 174–175 | 59b | B |
| 60a | H | CF₃ | H | H | H | phenyl | C | 103–104 | c | H |
| 61a | H | H | HOCH₂ | H | H | phenyl | C | 130–131 | 63a | K |
| 62a | H | H | CF₃ | H | H | formylamino | C | 179–180 | 62bᵈ | B |
| 63a | H | H | i-PrOCO | H | H | phenyl | C | 59–60 | 63b | B |
| 64a | H | Cl | Cl | H | H | phenyl | C | 190–192 | a | H |

TABLE 1-continued

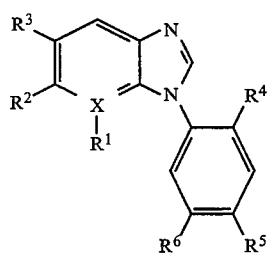

| No. | R¹ | R² | R³ | R⁴ | R⁵ | R⁶ | X | mp/°C. | Starting material | method |
|---|---|---|---|---|---|---|---|---|---|---|
| 65a | H | H | Cl | H | H | phenyl | C | 158–159 | 65b | B |
| 66a | H | H | CHO | H | H | phenyl | C | 170–172 | 61a | L |
| 67a | H | H | NO₂ | H | H | phenyl | C | 194–196 | 67b | B |
| 68a | H | H | AcOCH₂ | H | H | phenyl | C | 190–191 | 61a | M |
| 69a* | H | OMe | H | H | H | phenyl | C | 199–200 | e | H |
| 70a | H | H | OMe | H | H | phenyl | C | 111–112 | e | H |
| 71a | NO₂ | H | CF₃ | H | H | phenyl | C | 150–151 | 71b | B |
| 72a | NH₂ | H | CF₃ | H | H | phenyl | C | 70–71 | 71a | T |
| 73a* | H | H | MeOCH₂ | H | H | phenyl | C | 70–72 | 61a | N |
| 74a* | H | CH₃ | H | H | H | phenyl | C | 209–210 | 74b | B |
| 75a* | H | H | CH₃ | H | H | phenyl | C | 180–182 | 75b | B |
| 76a | H | H | HCONH | H | H | phenyl | C | 169–170 | 76b | B |
| 77a | H | Cl | H | H | H | phenyl | C | 151–152 | 77b | B |
| 78a* | H | H | CF₃ | H | H | 3-aminophenylsulphonyl | C | 188–191 | f | Y |
| 79a | H | H | H | H | H | 3-methoxyphenyl | C | oil | 17a | C |
| 80a | H | H | CF₃ | H | H | 3-hydroxyphenyl | C | 146–150 | 79a | I |
| 81a* | H | H | CH₃ | H | H | I | C | 227–229 | 81b | B |
| 82a | H | CH₃ | H | H | H | I | C | 233–235 | 82b | B |
| 83a | H | H | CF₃ | H | H | COOH | C | 243–245 | 83b | B |
| 85a | H | H | NO₂ | H | H | I | C | 203–204 | 85b | B |
| 86a | H | H | H | H | H | B(OH)2 | C | 208–212 | 86b | B |
| 87a* | H | H | CF₃ | H | H | B(OH)2 | C | 200–203 | 87b | B |

*HCl,
# = oxalate,
a. Starting from 3-bromobiphenyl and 5,6-dichlorobenzimidazole.
b. The single amino was formylated as the same time.
c. Starting from 3-bromobiphenyl and 5-trifluoromethylbenzimidazole. A mixture of the 5- and 6- substituted isomer was obtained and was separated by chromatography on silicagel with EtOAc/p.ether 1:4 as eluent.
d. The free amino group was formylated at the same time.
e. 69a and 70a was obtained as a mixture and could be separated by chromatography.
f. Compound 78a was prepared from 3-aminodiphenylsulfone according to methods Xb, U, B and Y in sequence.

TABLE 2

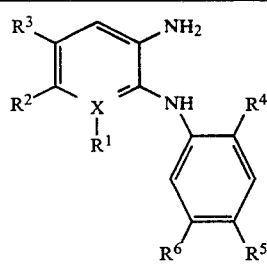

X is C in all of below examples

| No. | R¹ | R² | R³ | R⁴ | R⁵ | R⁶ | mp/°C. | Starting material | method |
|---|---|---|---|---|---|---|---|---|---|
| 1b | H | H | CN | H | H | Cl | 170–172 | 1c | T |
| 2b* | H | H | CF₃ | H | H | I | 182–185 | 2c | U |
| 5b* | H | H | F | H | I | H | 161–163 | 5c | U |
| 16b* | H | H | CF₃ | H | H | 3-phenoxy | 180–183 | 16c | T |
| 17b* | H | H | H | H | H | I | 200–202 | 17c | U |
| 19b | H | H | CF₃ | OMe | H | OMe | 156–160 | 19c | T |
| 26b* | H | H | CF₃ | H | H | phenethyl | 180–183 | 26c | T |
| 48b* | H | H | CF₃ | H | H | Br | 182–183 | 48c | U |
| 51b | H | H | F | H | H | I | ** | 51c | U |
| 58b* | H | H | CF₃ | H | H | CH3 | 200–210 | 58c | T |
| 59b | H | H | CF₃ | H | H | NO2 | 80–84 | 59c | U |
| 62b* | H | H | CF₃ | H | H | NH2 | >300 | 59c | T |
| 63b | H | H | i-PrOCO | H | H | phenyl | oil | 63c | T |
| 65b | H | H | Cl | H | H | phenyl | ** | 65c | T |
| 67b | H | H | NO2 | H | H | phenyl | ** | 67c | U |
| 71b | NO2 | H | CF₃ | H | H | phenyl | 90–93 | 71c | U |
| 74b | H | CH3 | H | H | H | phenyl | ** | 74c | T |

TABLE 2-continued

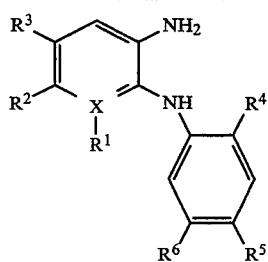

X is C in all of below examples

| No. | R¹ | R² | R³ | R⁴ | R⁵ | R⁶ | mp/°C. | Starting material | method |
|---|---|---|---|---|---|---|---|---|---|
| 75b | H | H | CH3 | H | H | phenyl | ** | 75c | T |
| 76b | H | H | NH2 | H | H | phenyl | 86–87 | 76c | T |
| 77b | H | Cl | H | H | H | phenyl | oil | 77c | T |
| 81b* | H | H | CH3 | H | H | I | 212–214 | 81c | U |
| 82b* | H | CH3 | H | H | H | I | 213–215 | 82c | U |
| 83b | H | H | CF3 | H | H | COOH | ** | 83c | T |
| 85b | H | H | NO2 | H | H | I | 175–180 | 85c | U |
| 86b | H | H | H | H | H | B(OH)2 | ** | 86c | T |
| 87b | H | H | CF3 | H | H | B(OH)2 | ** | 87c | T |

TABLE 3

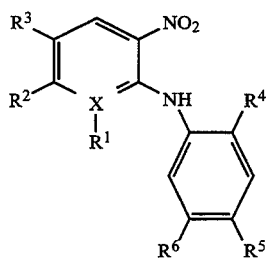

X is C in all of below examples

| No. | R¹ | R² | R³ | R⁴ | R⁵ | R⁶ | mp/°C. | method |
|---|---|---|---|---|---|---|---|---|
| 1c | H | H | CN | OH | H | Cl | 210–212 | V |
| 2c | H | H | CF3 | H | H | I | 98–101 | Xa |
| 5c | H | H | F | H | I | H | 122–125 | Xa |
| 16c | H | H | CF3 | H | H | 3-phenoxy | oil | Xa |
| 17c | H | H | H | H | H | I | 89–91 | Xb |
| 19c | H | H | CF3 | OMe | H | OMe | 93–95 | Xa |
| 26c | H | H | CF3 | H | H | phenethyl | ** | Xa |
| 48c | H | H | CF3 | H | H | Br | 84–88 | Xa |
| 51c | H | H | F | H | H | I | 117–120 | Xa |
| 58c | H | H | CF3 | H | H | CH3 | 100–102 | Xa |
| 59c | H | H | CF3 | H | H | NO2 | ** | Xa |
| 63c | H | H | i-PrOCO | H | H | phenyl | 90–93 | Xc |
| 65c | H | H | Cl | H | H | phenyl | 83–86 | Xc |
| 67c | H | H | NO2 | H | H | phenyl | 163–166 | Xc |
| 71c | NO2 | H | CF3 | H | H | phenyl | 138–139 | Xc |
| 74c | H | CH3 | H | H | H | phenyl | ** | Xc |
| 75c | H | H | CH3 | H | H | phenyl | ** | Xc |
| 77c | H | Cl | H | H | H | phenyl | oil | Xa |
| 81c | H | H | CH3 | H | H | I | 87–89 | Xb |
| 82c | H | CH3 | H | H | H | I | 109–111 | Xb |
| 83c | H | H | CF3 | H | H | COOH | 203–206 | Xa |
| 85c | H | H | NO2 | H | H | I | ** | Xb |
| 86c | H | H | H | H | H | B(OH)2 | 195–196 | Xc |
| 87c | H | H | CF3 | H | H | B(OH)2 | 228–229 | Xc |

Table 3. **was used for the next step without purification.

We claim:
1. A method of treating a disorder, which is responsive to the partial or complete blockade of calcium channels of the central nervous system of a living animal body, which comprises administering to such a living animal body, in need thereof a therapeutically-effective amount of a compound selected from those having the formula:

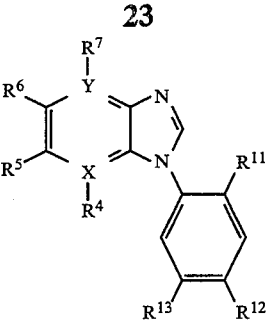

wherein
X is C;
Y is C;
R[11] is hydrogen, hydroxy, or alkoxy;
R[12] and R[13] are each independently hydrogen; halogen; $CF_3$; CN; OH; alkyl; cycloalkyl; cycloalkylalkyl; alkenyl; alkynyl; alkoxy; phenylalkyl; amino; nitro; sulphamoyl; piperidyl; pyrrolidinyl; acyl; $CO_2H$; $CO_2$-alkyl; CO-amino; NH-CO-alkyl; phenylsulphonyl which may be substituted with halogen, $CF_3$, CN, OH, alkyl, alkenyl, alkynyl, alkoxy, amino, or nitro; phenyloxy which may be substituted with halogen, $CF_3$, CN, OH, alkyl, alkenyl, alkynyl, alkoxy, amino, or nitro; phenylamino which may be substituted with halogen, $CF_3$, CN, OH, alkyl, alkenyl, alkynyl, alkoxy, amino, or nitro; or aryl which may be substituted one or more times with halogen, $CF_3$, CN, OH, alkyl, cycloalkyl, cycloalkylalkyl, alkenyl, alkynyl, alkoxy, phenoxy, phenylalkyl, amino, nitro, sulphamoyl, piperidyl, pyrrolidinyl, $CO_2H$, $CO_2$-alkyl, CO-amino, or NH-CO-alkyl; and R[4], R[5], R[6] and R[7] are each independently hydrogen; halogen; amino; nitro; CN; $CF_3$; COOH; COO-alkyl; alkyl; acyl; alkoxy; $-(CH_2)_n$-OH wherein n is 0, 1,2, or 3; $-(CH_2)_m$-O-alkyl wherein m is 0, 1,2, or 3; $-(CH_2)_o$-O-acyl wherein o is 0, 1,2, or 3;

or a pharmaceutically-acceptable addition salt thereof.

2. A method as in claim 1, wherein stroke, anoxia, ischemia, migraine, or epilepsy is treated.

3. A method as in claim 1, wherein psychosis, Parkinsonism, depression, epilepsy or any other convulsive disorder is treated.

4. A method of claim 1, wherein the compound employed is
1-[3-(3-aminophenyl)-phenyl]-5-trifluoromethyl-benzimidazole,
1-(3-phenylphenyl)-5-amino-benzimidazole,
1-[3-(3-amino-2-pyridyl)-phenyl]-5-trifluoromethyl-benzimidazole,
1-[3-(2-aminophenyl)-phenyl]-5-trifluoromethyl-benzimidazole,
1-[3-(4-methylphenyl)-phenyl]-benzimidazole,
1-[3-(3-aminophenyl)-phenyl]-benzimidazole,
1-[3-(3-methoxyphenyl)-phenyl]-5-amino-benzimidazole,
1-[3-(1-imidazolyl)-phenyl]-5-trifluoromethyl-benzimidazole,
1-(3-phenylphenyl)-5-methoxy-benzimidazole,
1-[3-(3-chlorphenyl)-phenyl]-benzimidazole,
1-[3-(3-trifluoromethyl-phenyl)-phenyl]-benzimidazole,
or a pharmaceutically-acceptable addition salt thereof.

5. The method of claim 1, wherein the active ingredient is administered in the form of a pharmaceutical composition thereof, in which it is present together with a pharmaceutically-acceptable carrier of diluent.

6. A method of treating the degenerative changes, connected with stroke, anoxia, ischemia, migraine, Parkinsonism, epilepsy or any other convulsive disorder, responsive to the partial or complete blockade of calcium channels of the central nervous system of a living animal body, which comprises administering to a living animal body in need thereof a therapeutically-effective calcium-channel-blocking amount of a calcium-channel-blocking compound as defined in claim 1.

7. A compound having the formula

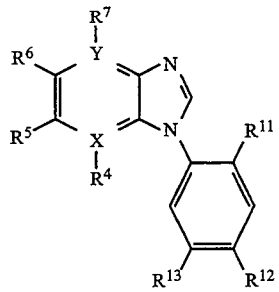

wherein
X is C;
Y is C;
R[11] is hydrogen, hydroxy, or alkoxy;
one of R[12] or R[13] is hydrogen; halogen; $CF_3$; CN; OH; alkyl; cycloalkyl; cycloalkylalkyl; alkenyl; alkynyl; alkoxy; phenylalkyl; amino; nitro; sulphamoyl; piperidyl; pyrrolidinyl; acyl; $CO_2H$; $CO_2$-alkyl; CO-amino; NH-CO-alkyl; and the other of R[12] or R[13] is phenylsulphonyl which may be substituted with halogen, $CF_3$, CN, OH, alkyl, alkenyl, alkynyl, alkoxy, amino, or nitro; phenyloxy which may be substituted with halogen, $CF_3$, CN, OH, alkyl, alkenyl, alkynyl, alkoxy, amino, or nitro; phenylamino which may be substituted with halogen, $CF_3$, CN, OH, alkyl, alkenyl, alkynyl, alkoxy, amino, or nitro; or aryl which may be substituted one or more times with halogen, $CF_3$, CN, alkyl, cycloalkyl, cycloalkylalkyl, alkenyl, alkynyl, alkoxy, phenoxy, phenylalkyl, amino, nitro, sulphamoyl, piperidyl, pyrrolidinyl, $CO_2H$, $CO_2$-alkyl, CO-amino, or NH-CO-alkyl; and R[4], R[5], R[6] and R[7] are each independently hydrogen; halogen; amino; nitro; CN; $CF_3$; COOH; COO-alkyl; alkyl; acyl; alkoxy; $-(CH_2)_n$-OH wherein n is 0, 1,2, or 3; $-(CH_2)_m$-O-alkyl wherein m is 0, 1,2, or 3; $-(CH_2)_o$-O-acyl wherein o is 0, 1,2, or 3; and that R[12] is different from phenyl when R[11], R[13], R[4], R[5], and R[7] are each hydrogen or when R[6] is hydrogen or amino ($NH_2$).

or a pharmaceutically-acceptable addition salt thereof.

8. A compound of claim 7 which is
1-[3-(3-aminophenyl)-phenyl]-5-trifluoromethyl-benzimidazole,
1-(3-phenylphenyl)-5-amino-benzimidazole,
1-[3-(3-amino-2-pyridyl)-phenyl]-5-trifluoromethyl-benzimidazole,
1-[3-(2-aminophenyl)-phenyl]-5-trifluoromethyl-benzimidazole,
1-[3-(4-methylphenyl)-phenyl]-benzimidazole,
1-[3-(3-aminophenyl)-phenyl]-benzimidazole, 1-[3-(3-methoxyphenyl)-phenyl]-5-amino-benzimidazole,
1-[3-(1-imidazolyl)-phenyl]-5-trifluoromethyl-benzimidazole,
1-(3-phenylphenyl)-5-methoxy-benzimidazole,
1-[3-(3-chlorphenyl)-phenyl]-benzimidazole,
1-[3-(3-trifluoromethyl-phenyl)-phenyl]-benzimidazole,
or a pharmaceutically-acceptable addition salt thereof.

9. A pharmaceutical composition comprising an effective amount of a compound of claim 7, together with at least one pharmaceutically-acceptable carrier or diluent.

* * * * *

UNITED STATES PATENT AND TRADEMARK OFFICE
CERTIFICATE OF CORRECTION

PATENT NO. : 5,360,809
DATED : November 1, 1994
INVENTOR(S) : Oskar Axelsson, Dan Peters, Elsebet O. Nielsen, Palle Christophersen It is certified that error appears in the above-indentified patent and that said Letters Patent is hereby corrected as shown below:

Column 2, line 22; "pipiridyl" should read -- piperidyl --
Column 2, line 33; "pipiridyi" should read -- piperidyl --
Column 3, line 33; "pipiri-" should read -- piperi- --
Column 3, line 45; "pipiridyl" should read -- piperidyl --
Column 4, line 40; "pipiri-" should read -- piperi- --
Column 4, line 54; "pipiridyl" should read -- piperidyl --
Column 4, line 62; "O is 0,1,2, or 3;" should read
    -- o is 0,1,2, or 3; --
Column 5, line 19; delete the word " a " (first occurrence)
Column 6, line 11; "1,2, 4-thiadiazol" should read
    -- 1,2, 4-thiadiazol-5-yl, --
Column 7, line 14; "3alkoxyphenyl," should read
    -- 3-alkoxyphenyl, --
Column 7, line 16; insert a space between "cycloalkyl" and the "1"
Column 7, line 62; "$^{45}CACl_2$" should read -- $^{45}CaCl_2$ --
Column 11, line 25; "3,biphenylyl)" should read
    -- -3-biphenylyl) --
Column 11, line 26; ")benzeneboronic" should read
    -- )-benzeneboronic --
Column 12, line 17; "-aminophe-" should read -- -amino- --

UNITED STATES PATENT AND TRADEMARK OFFICE
CERTIFICATE OF CORRECTION

PATENT NO. : 5,360,809
DATED : November 1, 1994
INVENTOR(S) : Oskar Axelsson, Dan Peters, Elsebet O. Nielsen, Palle Christophersen It is certified that error appears in the above-indentified patent and that said Letters Patent is hereby corrected as shown below:

```
Column 12, line 21; "NaHCO3" should read -- NaHCO₃ --
Column 13, line 45; "-5hydroxymethylben-" should read
    -- -5-hydroxymethylben-
Column 13, line 66; "-methoxymethyibenzimidazole"
    should read -- -methoxymethylbenzimidazole --
Column 19, approximately in the column
    (under table 1-continued, line 6 of the footnote labled "c";
    "silicagel" should read -- silica gel --
```

Signed and Sealed this

Fourteenth Day of February, 1995

Attest:

BRUCE LEHMAN

Attesting Officer     Commissioner of Patents and Trademarks